US012569429B2

(12) United States Patent (10) Patent No.: US 12,569,429 B2
Yagi et al. (45) Date of Patent: Mar. 10, 2026

(54) SKIN PENETRATION ENHANCER FOR ROYAL JELLY

(71) Applicant: Yamada Bee Company, Inc., Tomata-gun (JP)

(72) Inventors: Masayuki Yagi, Tomata-gun (JP); Yuka Maeda, Tomata-gun (JP)

(73) Assignee: YAMADA BEE COMPANY, INC., Tomata-gun (JP)

( * ) Notice: Subject to any disclaimer, the term of this patent is extended or adjusted under 35 U.S.C. 154(b) by 243 days.

(21) Appl. No.: 18/384,037

(22) Filed: Oct. 26, 2023

(65) Prior Publication Data

US 2024/0325291 A1 Oct. 3, 2024

(30) Foreign Application Priority Data

Mar. 31, 2023 (JP) ................................. 2023-058035

(51) Int. Cl.
| | |
|---|---|
| *A61K 8/98* | (2006.01) |
| *A61K 8/362* | (2006.01) |
| *A61K 8/365* | (2006.01) |
| *A61K 8/73* | (2006.01) |

(52) U.S. Cl.
CPC .............. *A61K 8/988* (2013.01); *A61K 8/362* (2013.01); *A61K 8/365* (2013.01); *A61K 8/73* (2013.01); *A61K 2800/40* (2013.01)

(58) Field of Classification Search
CPC ...................................................... A61K 8/988
See application file for complete search history.

(56) References Cited

FOREIGN PATENT DOCUMENTS

| | | | | | |
|---|---|---|---|---|---|
| CN | 109172388 | A | * | 1/2019 | ........... A61K 8/9717 |
| CN | 111110597 | A | | 5/2020 | |
| JP | 2007204418 | A | | 8/2007 | |
| JP | 2008007432 | A | | 1/2008 | |
| JP | 2011016726 | A | | 1/2011 | |
| JP | 2013075867 | A | | 4/2013 | |
| JP | 2015007123 | A | | 1/2015 | |
| JP | 2019019077 | A | | 2/2019 | |
| JP | 2022075265 | A | | 5/2022 | |
| JP | 2024086182 | A | | 6/2024 | |
| WO | 2019188774 | A1 | | 10/2019 | |
| WO | 2022255271 | A1 | | 12/2022 | |

OTHER PUBLICATIONS

Weaver et al., Heterogeneity of fatty acids from royal jelly. Nature (London, United Kingdom) (1960), 188, 938-9 (Year: 1960).*
Mintel GNPD, "Fast Skin Maker", Mar. 2018 ID: 5550029.
Mintel GNPD, "Power Serum", Mar. 2016, pID: 3820295.
Jafra, USA, "Extra Hydration Serum, ID#6205169, Mintel GNPD [online], [Accessed: Oct. 28, 2024], Internet URL : https://portal.mintel.com", Dec. 2018.
Honsha, Japan, "Milky Essence, ID#1491541, Mintel GNPD [online], [Accessed: Oct. 28, 2024], Internet URL : https://portal.mintel.com", Feb. 2011.
Sana, Japan, "Moisturizing Essence with 100% Fresh Royal Jelly, ID#331566, Mintel GNPD [online], [Accessed Oct. 28, 2024], Internet URL:https://portal.mintel.com", Feb. 2005.

* cited by examiner

*Primary Examiner* — Qiuwen Mi
(74) *Attorney, Agent, or Firm* — CANTOR COLBURN LLP

(57) ABSTRACT

A method for enhancing penetration of a royal jelly into a skin includes blending a carrageenan into a cosmetic composition including the royal jelly. A method for enhancing penetration of a royal jelly into a skin also includes applying a cosmetic composition including a carrageenan and the royal jelly on the skin. A method for producing a cosmetic composition including a royal jelly includes blending a carrageenan into the cosmetic composition for enhancing penetration of the royal jelly into a skin.

3 Claims, 2 Drawing Sheets

CONTROL        EXAMPLE        COMPARATIVE
                                    EXAMPLE

DEPTH 1
2
3
4
5
6
7
8
9
10

Min(1)                                              Max (30000)

SKIN PENETRATION ENHANCER FOR ROYAL JELLY

CROSS-REFERENCE TO RELATED APPLICATION

The present invention claims priority under 35 U.S.C. § 119 to Japanese Application, 2023-058035 filed on Mar. 31, 2023, the entire contents of which being incorporated herein by reference.

TECHNICAL FIELD

The present invention relates to a skin penetration enhancer for royal jelly.

BACKGROUND

It is known that royal jelly exhibits, when applied on the skin, a skin aging prevention effect, a cosmetic effect leading to moist and firm skin, and the like (for example, Japanese Unexamined Patent Publication No. 2007-204418). These cosmetic effects are believed to be brought by fatty acids characteristic of royal jelly, such as 10-hydroxy-2-decenoic acid in particular. Therefore, in order to have the cosmetic effect of royal jelly fully exhibited, particularly the skin penetrability of the fatty acids characteristic of royal jelly is important. Japanese Unexamined Patent Publication No. 2015-007123 discloses a skin preparation for external use including a royal jelly extract as a skin activating component, and it is described that as this skin preparation for external use stably retains moisture on the skin for a long time period, the penetrability of the skin activating component into the skin is elevated.

SUMMARY

It is an object of the present invention to provide a new skin penetration enhancer for royal jelly.

According to the previous studies conducted by the inventors of the present invention, it was found that an (acrylates/(C10-30) alkyl acrylate) crosspolymer and an (ammonium acryloyldimethyltaurate/methacrylic acid beheneth-25) crosspolymer have an action of enhancing the penetration of royal jelly into the skin (Japanese Patent Application No. 2022-201184 (not published)). The inventors of the present invention conducted further studies in order to achieve the above-described object, and as a result, the inventors newly found that carrageenan, which is used as a cosmetic additive, enhances the penetration of royal jelly into the skin, thus completing the present invention.

That is, the present invention relates to, for example, the following inventions.

[1] A skin penetration enhancer for a royal jelly, comprising a carrageenan as an active ingredient.

[2] The skin penetration enhancer according to [1], wherein the royal jelly comprises saturated fatty acids and/or unsaturated fatty acids.

[3] The skin penetration enhancer according to [2], wherein the saturated fatty acids comprise 10-hydroxydecanoic acid.

[4] The skin penetration enhancer according to [2], wherein the unsaturated fatty acids comprise at least one of 10-hydroxy-2-decenoic acid, decenedioic acid, or sebacic acid.

[5] A cosmetic composition comprising the skin penetration enhancer according to any one of [1] to [4] and a royal jelly.

[6] A method for producing a cosmetic composition comprising a royal jelly, the method comprising blending the skin penetration enhancer according to any one of [1] to [4] and the royal jelly into a cosmetic composition.

[7] A method for enhancing penetration of a royal jelly into a skin, the method comprising blending the skin penetration enhancer according to any one of [1] to [4] into a cosmetic composition comprising the royal jelly.

[8] A method for enhancing penetration of a royal jelly into a skin, the method comprising applying the cosmetic composition according to [5] on the skin.

[9] A method for enhancing penetration of a royal jelly into a skin, the method comprising blending a carrageenan into a cosmetic composition comprising the royal jelly.

[10] The method according to [9], wherein the royal jelly comprises saturated fatty acids and/or unsaturated fatty acids.

[11] The method according to [10], wherein the saturated fatty acids comprise 10-hydroxydecanoic acid.

[12] The method according to [10], wherein the unsaturated fatty acids comprise at least one of 10-hydroxy-2-decenoic acid, decenedioic acid, or sebacic acid.

[13] A method for enhancing penetration of a royal jelly into a skin, the method comprising applying a cosmetic composition comprising a carrageenan and the royal jelly on the skin.

[14] The method according to [13], wherein the royal jelly comprises saturated fatty acids and/or unsaturated fatty acids.

[15] The method according to [14], wherein the saturated fatty acids comprise 10-hydroxydecanoic acid.

[16] The method according to [14], wherein the unsaturated fatty acids comprise at least one of 10-hydroxy-2-decenoic acid, decenedioic acid, or sebacic acid.

[17] The method according to any one of [13] to [16], wherein a content of the carrageenan in the cosmetic composition is 0.01% by mass or more and 20% by mass or less, with respect to the total amount of the cosmetic composition.

[18] The method according to any one of [13] to [17], wherein a content of the royal jelly in the cosmetic composition is 0.10% by mass or more and 20% by mass or less, with respect to the total amount of the cosmetic composition.

[19] A method for producing a cosmetic composition comprising a royal jelly, the method comprising blending a carrageenan into the cosmetic composition for enhancing penetration of the royal jelly into a skin.

[20] The production method according to [19], wherein the royal jelly comprises saturated fatty acids and/or unsaturated fatty acids.

[21] The production method according to [20], wherein the saturated fatty acids comprise 10-hydroxydecanoic acid.

[22] The production method according to [20], wherein the unsaturated fatty acids comprise at least one of 10-hydroxy-2-decenoic acid, decenedioic acid, or sebacic acid.

[23] The method according to any one of [9] to [12], wherein the royal jelly is a filtrate obtained by filtering enzymatically treated royal jelly solution through a filter having a pore size of 3 μm, and wherein the cosmetic composition comprises butylene glycol, pentylene glycol, and phenoxyethanol.

[24] The method according to any one of [13] to [18], wherein the royal jelly is a filtrate obtained by filtering enzymatically treated royal jelly solution through a filter having a pore size of 3 μm, and wherein the cosmetic composition comprises butylene glycol, pentylene glycol, and phenoxyethanol.

[25] The method according to any one of [19] to [22], wherein the royal jelly is a filtrate obtained by filtering enzymatically treated royal jelly solution through a filter having a pore size of 3 μm, and wherein the cosmetic composition comprises butylene glycol, pentylene glycol, and phenoxyethanol.

According to the skin penetration enhancer of the present invention, a cosmetic effect of a cosmetic composition including royal jelly can be heightened by enhancing the penetration of royal jelly into the skin.

DETAILED DESCRIPTION

Figure 1:
FIG. 1 shows the results of imaging mass spectrometry (MS) showing the penetrability of 10-hydroxy-2-decenoic acid into the skin.

Embodiments for carrying out the present invention will be described in detail below. However, the present invention is not intended to be limited to the following embodiments.

The skin penetration enhancer for royal jelly of the present invention includes a carrageenan as an active ingredient.

Carrageenan is a carbohydrate obtained from red algae of the family Gigartinaceae, the family Solieriaceae, and the like, and is specifically a linear sulfated polysaccharide composed of a repeating unit of galactose and 3,6-anhydrogalactose linked by alternate bonding of α1-3 and β1-4- glycosidic bonds. It is known that there are mainly three kinds of carrageenan, namely, lambda-carrageenan, kappa-carrageenan, and iota-carrageenan. The carrageenan according to the present invention may be any of lambda-carrageenan, kappa-carrageenan, iota-carrageenan, and any combinations of these.

Regarding the carrageenan, a product obtained by performing extraction from red algae and the like according to a conventionally known method (for example, the method described in Japanese Unexamined Patent Publication No. 2009-1700) and optional purification may be used, or a commercially available product may be used. Examples of a commercially available carrageenan product include purified carrageenan (for example, GENUGEL (trademark) Carrageenan Type CJ; Sansho Co., Ltd.). The purified carrageenan may include other components such as additives in addition to carrageenan, for example, sucrose. The mass ratio of carrageenan and sucrose is not particularly limited, and the mass ratio may be, for example, 1 to 10:1 to 10, or may be, for example, 2:1, 7:3, 6:4, or 1:1.

Carrageenan is a cosmetic component known as a thickener or a gelling agent; however, the effect of enhancing the penetration of royal jelly into the skin has not been known yet.

The enhancement of penetration of royal jelly into the skin means that the components included in royal jelly, particularly active ingredients having cosmetic effects, for example, components such as saturated fatty acids and unsaturated fatty acids, penetrate more deeply into the horny layer of the skin as compared to the case where a skin penetration enhancer is not included. Here, examples of the saturated fatty acids include 10-hydroxydecanoic acid, 8-hydroxyoctanoic acid, 12-hydroxydodecanoic acid, 3,10-dihydroxydecanoic acid, and capric acid, and examples of the unsaturated fatty acids include 10-hydroxy-2-decenoic acid, decenedioic acid, sebacic acid, and trans-2-decenoic acid. Preferred examples of the saturated fatty acids include 10-hydroxydecanoic acid, and preferred examples of the unsaturated fatty acids include 10-hydroxy-2-decenoic acid, decenedioic acid, and sebacic acid.

The enhancement of penetration of royal jelly into the skin can be evaluated by analyzing the components included in royal jelly, particularly components such as saturated fatty acids and unsaturated fatty acids, for example, by the method described in the Examples. Specifically, a method of applying a composition including royal jelly and a skin penetration enhancer on the skin, collecting a horny layer sample after a predetermined time (for example, after 30 minutes, after 1 hour, or after 2 hours) by performing a tape stripping test, and detecting royal jelly that has attached to the tape, may be mentioned.

The method for detecting the royal jelly components that have penetrated into the horny layer is not particularly limited, and for example, the royal jelly components may be detected by imaging using a mass spectrometer as will be described in the Examples of the present application.

(Royal Jelly)

Royal jelly is a milky white gelatinous substance made by 3- to 12-day-old worker bees among honeybees through mixing of a secretion secreted from the hypopharyngeal gland and mandibular gland. Examples of major biologically active components in royal jelly include organic acids such as the saturated fatty acids and unsaturated fatty acids unique to royal jelly, a protein, an amino acid, a peptide, a lipid, sugars, vitamins such as vitamin Bs, a folic acid, a nicotinic acid, and a pantothenic acid, and various type of minerals.

Examples of the royal jelly according to the present invention include raw royal jelly, dried royal jelly, a dried royal jelly powder, an enzymatically treated royal jelly, a royal jelly extract, and a royal jelly fermentation product. In addition, a place of production of royal jelly is not limited, and may be any of European countries, Oceanian countries, the U.S.A., Brazil, Japan, China, and other Asian countries and the like.

The dried royal jelly powder is a product obtained by drying and powderizing raw royal jelly. As a drying method, any known method that is employed in general food processing, such as natural drying, e.g., ventilation drying and solar drying, forced drying that involves heating with electricity or the like for drying, and freeze-drying can be used. Preferably freeze-drying is used.

The enzymatically treated royal jelly is a product obtained by treating royal jelly with a proteolytic enzyme (protease). The preferred enzymatically treated royal jelly is a low-allergenized enzymatically treated royal jelly in which an allergic reaction caused by the proteins included in royal jelly is suppressed by a protease treatment. Therefore, the enzymatically treated royal jelly may include, in addition to a protease-degradation product of the proteins included in royal jelly, organic acids such as the above-described saturated fatty acids and unsaturated fatty acids, a lipid, sugars, vitamins, and various type of minerals.

The royal jelly to be used for the production of the enzymatically treated royal jelly is not particularly limited, and examples include raw royal jelly, a royal jelly powder obtained by drying and powderizing raw royal jelly, and a product obtained by extracting raw royal jelly using water, water-containing ethanol, or the like.

The production of the enzymatically treated royal jelly can be carried out by treating a royal jelly raw material with an enzyme having at least an endopeptidase action, an enzyme having at least an exopeptidase action, and/or an enzyme having an endopeptidase action and an exopeptidase action.

Examples of protease having at least endopeptidase activity include animal-derived (for examples, trypsin and chymotrypsin), plant-derived (for example, papain), microbial-derived (for example, lactic acid bacteria, yeast, fungi, *Bacillus subtilis*, and Actinomycetes) endopeptidases.

Examples of protease having at least an exopeptidase activity include carboxypeptidases, aminopeptidases, microbial-derived (for example, lactic acid bacteria, bacteria of the genus *Aspergillus* and *Rhizopus* etc.) exopeptidases, pancreatin also having endopeptidase activity, and pepsin.

Among such various enzymes, preferred examples of the enzyme having both exopeptidase activity and endopeptidase activity can include *Streptomyces griseus*-produced peptidase (trade name: ACTINASE AS), *Aspergillus oryzae*-produced peptidase (trade name: PROTEASE A, FLAVOURZYME, PROTEAX), *Aspergillus melleus*-produced peptidase (trade name: PROTEASE P), and preferred examples of the enzyme having exoprotease activity can include *Aspergillus oryzae*-produced peptidase (for example, UMAMIZYME G, Promod 192P, Promod 194P, SUMIZYME FLAP), *Aspergillus sojae*-produced peptidase (trade name: STERNZYME B15024), the genus *Aspergillus*-produced peptidase (trade name: KOKULASE P), and *Rhizopus oryzae*-produced peptidase (trade name: PEPTIDASE R). Furthermore, preferred examples of an enzyme having endoprotease activity can include *Bacillus subtilis*-produced peptidase (trade name: ORIENTASE 22BF, NUCLEICIN), *Bacillus licheniformis*-produced peptidase (trade name: ALCALASE), *Bacillus stearothermophilus*-produced peptidase (trade name: PROTEASE S), *Bacillus amyloliquefaciens*-produced peptidase (trade name: NEUTRASE), and the genus *Bacillus*-produced peptidase (trade name: PROTAMEX).

An enzymatic treatment for reducing allergenicity of royal jelly can be carried out according to, for example, the descriptions of Japanese Unexamined Patent Publication No. 2007-295919 and Japanese Unexamined Patent Publication No. 2007-295920.

The royal jelly extract is a product obtained by extracting royal jelly (including raw royal jelly, a dried product, and a pulverized product) using water, water-containing ethanol, or the like.

The royal jelly fermentation product can be produced by a conventional method by using microorganisms such as yeast and lactic acid bacteria.

Regarding the royal jelly, a commercially available one may be used. Specific examples of the royal jelly include, Royal Jelly FD Powder (Nakahara Co., Ltd.), Royal Jelly Extract SF (MATSUURA YAKUGYO CO., LTD.), Deproteinized Royal Jelly Powder F (MARUZEN PHARMACEUTICALS CO., LTD.), and Deproteinized Royal Jelly Extract (API Co., Ltd.).

The royal jelly is not particularly limited as long as it has, for example, a skin aging prevention effect and a cosmetic effect leading to moist and firm skin; however, it is preferable that the royal jelly includes saturated fatty acids and/or unsaturated fatty acids, it is preferable that the saturated fatty acids include 10-hydroxy-2-decenoic acid, and it is preferable that the unsaturated fatty acids include at least one of 10-hydroxydecanoic acid, decenedioic acid, or sebacic acid. The skin penetration enhancer of the present invention can be used for a skin preparation for external use, a cosmetic composition, and the like, all of which contain royal jelly.

(Cosmetic Composition)

The cosmetic composition of the present invention includes the skin penetration enhancer for royal jelly of the present invention, and royal jelly.

The content of carrageenan in the cosmetic composition may be any amount (effective amount) that can exhibit the skin penetration enhancing action for royal jelly, and for example, the content may be 0.01% by mass or more, 0.10% by mass or more, 0.3% by mass or more, 0.4% by mass or more, 0.5% by mass or more, 1% by mass or more, 2% by mass or more, 3% by mass or more, or 5% by mass or more, and may be 20% by mass or less, 15% by mass or less, 10% by mass or less, 8% by mass or less, 5% by mass or less, 3% by mass or less, 2% by mass or less, 1% by mass or less, or 0.5% by mass or less, with respect to the total amount of the cosmetic composition.

The content of royal jelly in the cosmetic composition is not particularly limited as long as the content is in the range that allows royal jelly to exhibit a cosmetic effect, and for example, the content may be 0.1% by mass or more, 0.5% by mass or more, 1% by mass or more, 1.5% by mass or more, 2% by mass or more, 3% by mass or more, 5% by mass or more, 8% by mass or more, 10% by mass or more, or 15% by mass or more, and may be 20% by mass or less, 15% by mass or less, 10% by mass or less, 8% by mass or less, 5% by mass or less, 3% by mass or less, 2% by mass or less, 1% by mass or less, or 0.5% by mass or less, with respect to the total amount of the cosmetic composition.

The cosmetic composition may be in the form of any of a solid, a liquid, a paste, and the like. The cosmetic product may be a medicinal cosmetic product (that is, a quasi-drug). The cosmetic composition includes all kinds of cosmetic compositions that can be applied to sites such as skin, mucous membrane, body hair, head hair, scalp, nails, teeth, facial skin, and lips of animals (particularly, humans). Among these, from the viewpoint of enhancing the penetration of royal jelly, the cosmetic composition is preferably a cosmetic composition that is applied to the skin of the whole body, for example, face, scalp, and lips.

The cosmetic composition may include cosmetically acceptable components, in addition to the skin penetration enhancer of the present invention and royal jelly. Examples of the cosmetically acceptable components include a whitening agent, a moisturizer, an antioxidant, an oily component, an ultraviolet absorber, a surfactant, a thickener, an alcohol, a powder component, a color material, an aqueous component, water, and various skin nutrients.

The dosage form of the cosmetic composition may be, for example, a solubilized system, an emulsified system, a powdered system, an oily liquid system, a gel system, an ointment system, an aerosol system, a water-oil bilayer system, or a water-oil-powder trilayer system. The cosmetic product may be, for example, a basic skin care product such as a facial cleanser, a skin lotion, an emulsion, a cream, a gel, an essence, a beauty serum, a pack, a mask, a mist, or a UV-blocking cosmetic product; a makeup cosmetic product such as a foundation, a lipstick, a cheek rouge, an eyeshadow, an eyeliner, or a mascara; a facial cleanser, a massage agent, a cleansing agent, an after-shave lotion, a pre-shave lotion, a shaving cream, a body soap, a soap, a shampoo, a hair conditioner, a hair treatment, a hair styling material, a hair tonic agent, a hair mist, a hair foam, a hair liquid, a hair gel, a hair spray, a hair growth promoter, an antiperspirant, a bath additive, a mouthwash, an oral cosmetic product, a toothpaste, a hand cream, or a hand soap.

The production method for the above-described cosmetic composition is not particularly limited, and any known method can be appropriately adopted. For example, a cosmetic composition to be used for the above-described purpose can be obtained by mixing the above-described skin penetration enhancer and royal jelly into an intermediate product or a final product obtained in the production process for a cosmetic product.

The method for producing the cosmetic composition including the royal jelly according to an embodiment is method including blending the carrageenan into the cosmetic composition for enhancing penetration of the royal jelly into the skin. The royal jelly may include saturated fatty acids and/or unsaturated fatty acids, it is preferable that the saturated fatty acids include 10-hydroxy-2-decenoic acid, and it is preferable that the unsaturated fatty acids include at least one of 10-hydroxydecanoic acid, decenedioic acid, or sebacic acid.

(Method for Enhancing Penetration of Royal Jelly into Skin)

The method for enhancing the penetration of royal jelly into the skin according to an embodiment includes blending the skin penetration enhancer of the present invention into a cosmetic composition including royal jelly. By blending the skin penetration enhancer of the present invention into a cosmetic composition including royal jelly, when the resulting cosmetic composition is applied on the skin, the penetration of the royal jelly included in the cosmetic composition into the skin is enhanced due to the presence of the skin penetration enhancer of the present invention, as compared with a cosmetic composition that does not include the skin penetration enhancer of the present invention.

The method for enhancing the penetration of the royal jelly into the skin according to another embodiment is the method includes blending the carrageenan into the cosmetic composition comprising the royal jelly for enhancing penetration of the royal jelly into the skin. The royal jelly may include saturated fatty acids and/or unsaturated fatty acids, it is preferable that the saturated fatty acids include 10-hydroxy-2-decenoic acid, and it is preferable that the unsaturated fatty acids include at least one of 10-hydroxydecanoic acid, decenedioic acid, or sebacic acid.

A method for enhancing the penetration of royal jelly into the skin according to a further embodiment includes applying the cosmetic composition of the present invention on the skin. By applying the cosmetic composition of the present invention on the skin, the penetration of the royal jelly included in the cosmetic composition into the skin is enhanced due to the presence of the skin penetration enhancer of the present invention, as compared with a cosmetic composition that does not include the skin penetration enhancer of the present invention.

The method for enhancing the penetration of the royal jelly into the skin according to a further other embodiment is the method includes applying the cosmetic composition including the carrageenan and the royal jelly on the skin. The royal jelly may include saturated fatty acids and/or unsaturated fatty acids, it is preferable that the saturated fatty acids include 10-hydroxy-2-decenoic acid, and it is preferable that the unsaturated fatty acids include at least one of 10-hydroxydecanoic acid, decenedioic acid, or sebacic acid.

EXAMPLES

Hereinafter, Examples will be described below in order to describe the present application more specifically. However, the present application is not intended to be limited to the following Examples.

(Preparation of Enzymatically Treated Royal Jelly Extract)

An enzymatically treated royal jelly extract was prepared by treating raw royal jelly according to the method described in WO 2020/196065 A1. Specifically, 400 ml of ion-exchanged water was added to 474 g of raw royal jelly, and the mixture was stirred until the mixture became uniform to prepare a royal jelly diluted solution. A 2 N aqueous solution of NaOH was added thereto to adjust the pH of the royal jelly diluted solution to 7.8. Next, a solution obtained by dissolving 4.75 g of PROTEAX (Amano Enzyme Inc.), which has both the endopeptidase action and the exopeptidase action, in 20 mL of ion-exchanged water was added to the royal jelly diluted solution, and ion-exchanged water was further added thereto so that the total amount reached 980 g. The reaction mixture was allowed to react at 50° C. (constant temperature water tank) for 2 hours while being stirred with a propeller to perform hydrolysis. The temperature of the constant temperature water tank was raised to 80° C., and the mixture was stirred for 15 minutes to deactivate the protease. The obtained enzymatically treated royal jelly solution was filtered through a filter having a pore size of 3 m, and an enzymatically treated royal jelly solution was obtained. Butylene glycol, pentylene glycol, phenoxyethanol, and purified water were added thereto so that the concentration of the enzymatically treated royal jelly solution was 2.5% by weight, and an enzymatically treated royal jelly extract was obtained.

(Preparation of Cosmetic Composition of Example)

A cosmetic composition containing royal jelly and carrageenan was prepared as a cosmetic composition of Example.

The cosmetic composition of Example was prepared by mixing the enzymatically treated royal jelly extract, GENU-GEL (tradename) Carrageenan type CJ as a skin penetration enhancer, and other raw materials described in Table 1 at predetermined proportions. The composition of the obtained cosmetic composition is shown in Table 1. Incidentally, sucrose is an additive included in GENUGEL (tradename) Carrageenan type CJ (carrageenan:sucrose=7:3).

TABLE 1

| Component | Proportion (% by weight) |
|---|---|
| Water | 83.90 |
| Butylene glycol | 10.50 |
| Pentylene glycol | 3.00 |
| Carrageenan | 0.35 |
| Sucrose | 0.15 |
| Enzymatically treated royal jelly extract | 1.50 |
| Phenoxyethanol | 0.60 |

(Preparation of Cosmetic Composition of Comparative Example)

A cosmetic composition of Comparative Example was prepared by mixing the enzymatically treated royal jelly extract and other raw materials described in Table 2 at predetermined proportions. The composition of the obtained cosmetic composition of Comparative Example is shown in Table 2.

TABLE 2

| Component | Proportion (% by weight) |
|---|---|
| Water | 83.90 |
| Butylene glycol | 10.50 |
| Pentylene glycol | 3.00 |

TABLE 2-continued

| Component | Proportion (% by weight) |
|---|---|
| Na alginate | 0.50 |
| Enzymatically treated royal jelly extract | 1.50 |
| Phenoxyethanol | 0.60 |

(Skin Penetration Test)

The skin penetrability of the cosmetic compositions of Example and Comparative Example were evaluated by the following method. First, a sample was prepared by a tape stripping test. The forearm part of one volunteer was cleaned and left to stand at room temperature for 15 minutes. Each of the cosmetic compositions of Example and Comparative Example in an amount of 30 mg/cm$^2$ was applied on a square-shaped skin of 6.25 cm$^2$ in the forearm part and was left to stand for 2 hours. The applied part was cleaned and left to stand for 15 minutes. Thereafter, a circular-shaped tape (D-Squame sampling discs (CUDERM)) having a diameter of 2 cm was stuck to the applied skin part, the tape was pressed for one minute, subsequently the circular-shaped tape was peeled off, the center part of the circle of the peeled circular-shaped tape was cut into a width of 5 mm, and this was used as a sample for imaging mass spectrometry (imaging MS). Similarly, the operation of sticking a circular-shaped tape to the applied skin part and peeling the tape therefrom was further repeated nine times, and a total of ten samples for imaging MS prepared by cutting the central part of the circle of the circular-shaped tape into a width of 5 mm were obtained. Ten samples as controls were also prepared in the same manner for the skin before applying the cosmetic composition to be tested.

Imaging MS was performed by using DESI Xevo G2 XS QTof (Waters Corporation). The attached amounts of the 10-hydroxy-2-decenoic acid and 10-hydroxydecanoic acid included in royal jelly in each sample were quantitatively determined by detecting m/z 185.1172 and m/z 187.1328 ions.

Figure 2:
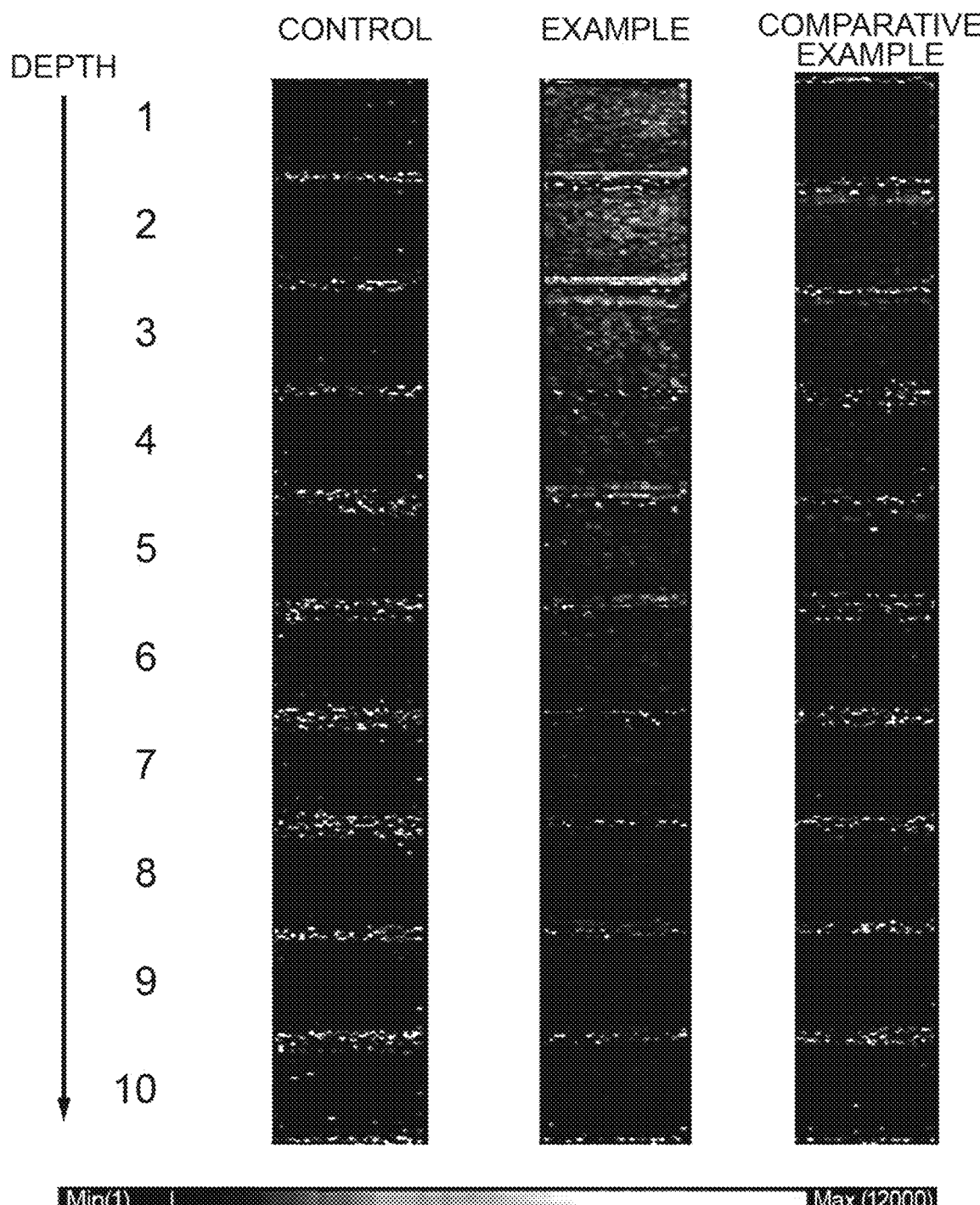
FIG. 2 shows the results of imaging MS showing the penetrability of 10-hydroxydecanoic acid into the skin.

FIG. 1 and FIG. 2 show the results of imaging MS indicating the penetrability of 10-hydroxy-2-decenoic acid and 10-hydroxydecanoic acid into the skin, respectively. From FIG. 1 and FIG. 2, regarding the control and the cosmetic composition containing Na alginate of Comparative Example, 10-hydroxy-2-decenoic acid and 10-hydroxydecanoic acid were not detected from any of the tapes, while regarding the cosmetic composition containing carrageenan of Example, 10-hydroxy-2-decenoic acid and 10-hydroxydecanoic acid were detected up to the fourth sheet of tape. From this, it was proved that the penetration of royal jelly into the skin can be enhanced by adding carrageenan.

What is claimed is:

1. A method for enhancing penetration of a royal jelly into a skin, the method comprising blending a carrageenan into a cosmetic composition comprising the royal jelly, butylene glycol, pentylene glycol, and phenoxyethanol, wherein the royal jelly is a filtrate obtained by filtering enzymatically treated royal jelly solution through a filter having a pore size of 3 μm.

2. A method for enhancing penetration of a royal jelly into a skin, the method comprising applying a cosmetic composition on the skin, the cosmetic composition comprising a carrageenan, butylene glycol, pentylene glycol, phenoxyethanol, and the royal jelly, wherein the royal jelly is a filtrate obtained by filtering enzymatically treated royal jelly solution through a filter having a pore size of 3 μm.

3. A method for producing a cosmetic composition comprising a royal jelly, the method comprising blending a carrageenan into the cosmetic composition for enhancing penetration of the royal jelly into a skin, wherein the royal jelly is a filtrate obtained by filtering enzymatically treated royal jelly solution through a filter having a pore size of 3 μm, and wherein the cosmetic composition further comprises butylene glycol, pentylene glycol, and phenoxyethanol.

* * * * *